US012593981B2

(12) United States Patent
Perlbarg

(10) Patent No.: US 12,593,981 B2
(45) Date of Patent: Apr. 7, 2026

(54) METHOD FOR DETERMINATION OF AN INDICATOR REPRESENTATIVE OF A CHANGE IN THE BRAIN OF AN INDIVIDUAL CAUSED BY A DEMYELINATING OR RELATED DISEASE, AFFECTING THE STATE OF THE MYELIN OF THE BRAIN

(71) Applicant: BRAINTALE, Strasbourg (FR)

(72) Inventor: Vincent Perlbarg, Paris (FR)

(73) Assignee: BRAINTALE, Strasbourg (FR)

( * ) Notice: Subject to any disclaimer, the term of this patent is extended or adjusted under 35 U.S.C. 154(b) by 238 days.

(21) Appl. No.: 18/683,931

(22) PCT Filed: Aug. 19, 2022

(86) PCT No.: PCT/EP2022/073240
§ 371 (c)(1),
(2) Date: Feb. 15, 2024

(87) PCT Pub. No.: WO2023/021201
PCT Pub. Date: Feb. 23, 2023

(65) Prior Publication Data
US 2024/0350012 A1     Oct. 24, 2024

(30) Foreign Application Priority Data
Aug. 20, 2021     (FR) ...................................... 2108808

(51) Int. Cl.
*G01V 3/00*     (2006.01)
*A61B 5/00*     (2006.01)
(Continued)

(52) U.S. Cl.
CPC ............ *A61B 5/0042* (2013.01); *A61B 5/055* (2013.01); *A61B 5/7282* (2013.01);
(Continued)

(58) Field of Classification Search
CPC .......... G01R 33/56341; G01R 33/4824; G01R 33/5608
(Continued)

(56) References Cited

U.S. PATENT DOCUMENTS

2015/0379713 A1     12/2015     Puybasset et al.

FOREIGN PATENT DOCUMENTS

WO     WO-2014060695 A2 *     4/2014     ........... A61B 5/7264

OTHER PUBLICATIONS

International Search Report as issued in International Patent Application No. PCT/EP2022/073240, dated Dec. 2, 2022.
(Continued)

*Primary Examiner* — Walter L Lindsay, Jr.
*Assistant Examiner* — Frederick Wenderoth
(74) *Attorney, Agent, or Firm* — CUSHMAN PARTNERS

(57) ABSTRACT
A method for determination of an indicator representative of a change in the brain caused by a demyelinating disease, the method including, for each region of interest of the brain, determining a regional coefficient of one of the following diffusion coefficients: the radial diffusion, the axial diffusion, the mean diffusion, the anisotropy fraction, or a combination of several of these coefficients, the regional coefficients being determined from a diffusion MRI image; determining a number of changed regions, for which a condition relating to the value of the regional diffusion coefficient of each region is satisfied; and determining the indicator in accordance with the number of changed regions.

12 Claims, 4 Drawing Sheets

10

(51) Int. Cl.
   *A61B 5/055*        (2006.01)
   *G01R 33/48*        (2006.01)
(52) U.S. Cl.
   CPC ........ *A61B 5/7485* (2013.01); *G01R 33/4806*
                    (2013.01); *A61B 2576/026* (2013.01)
(58) Field of Classification Search
   USPC ....................................................... 324/309
   See application file for complete search history.

(56)                    References Cited

OTHER PUBLICATIONS

Dr Aung, W. Y., et al., "Diffusion tensor MRI as a biomarker in axonal and myelin damage," Imaging in Medicine, vol. 5, No. 5, Oct. 2013, XP055916484, Retrieved from the Internet: URL: https://www.ncbi.nlm.nih.gov/pmc/articles/PMC4004089/pdf/nihms560933.pdf, [retrieved on Nov. 23, 2022], 28 pages.
Alexander, A. L., et al., "Diffusion Tensor Imaging of the Brain," Neurotherapeutics: The Journal of the American Society for Experimental NeuroTherapeutics, vol. 4, No. 3, Jul. 2007, XP055916523, Retrieved from the Internet: URL:https://www.ncbi.nlm.nih.gov/pmc/articles/PMC2041910/pdf/13311_2011_ArtiArt_40300316.pdf, 14 pages.

* cited by examiner

[Fig. 1]
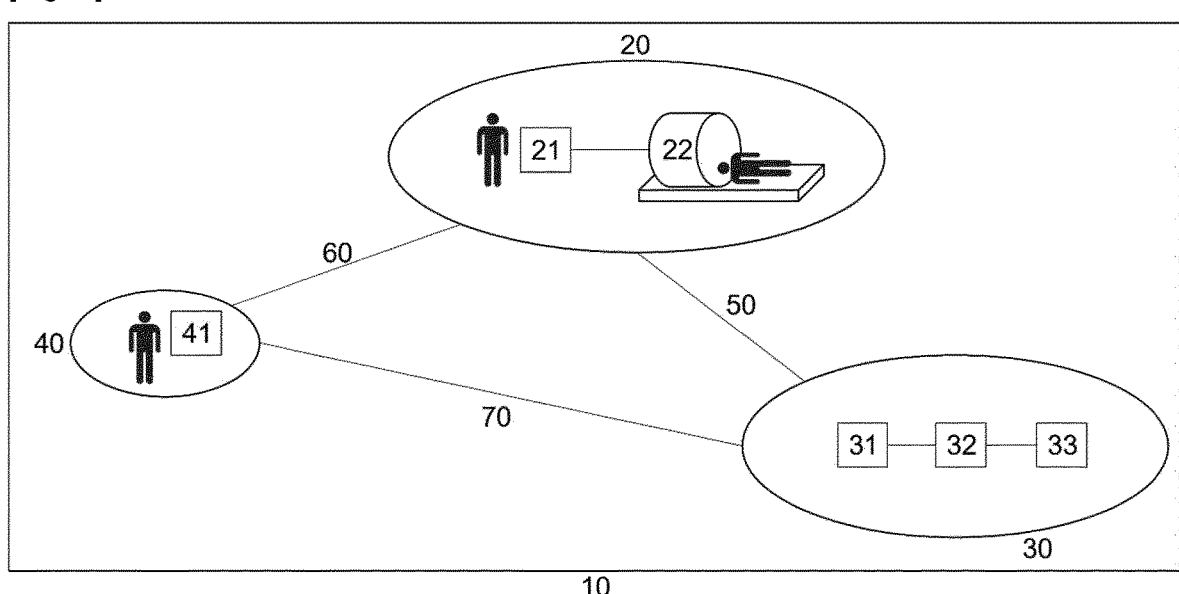
[Fig. 2]
100
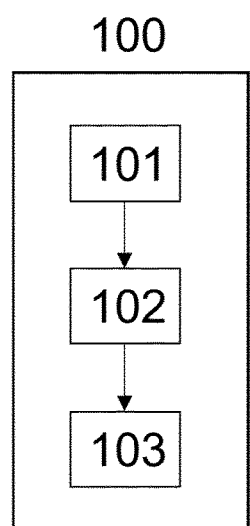

[Fig. 3]
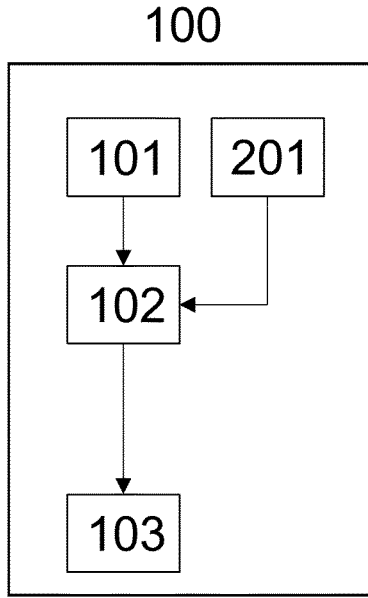
[Fig. 4]
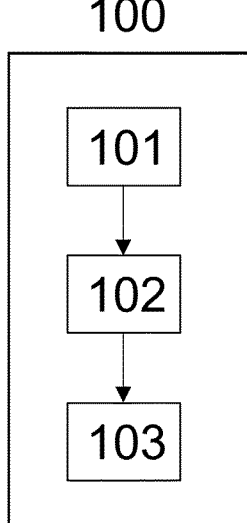

[Fig. 5]
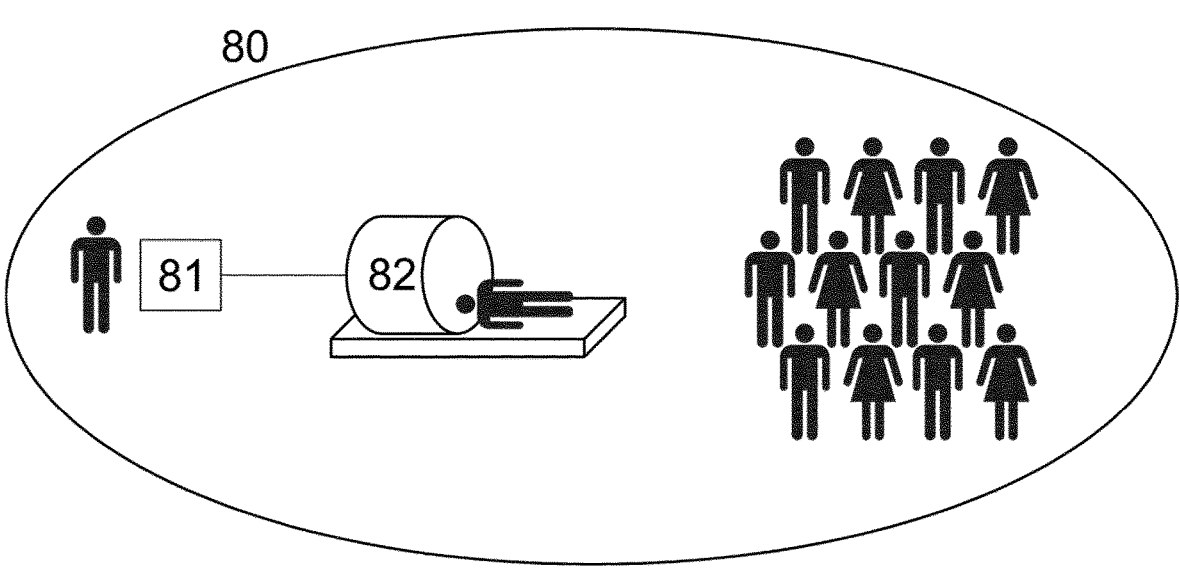
[Fig. 6]
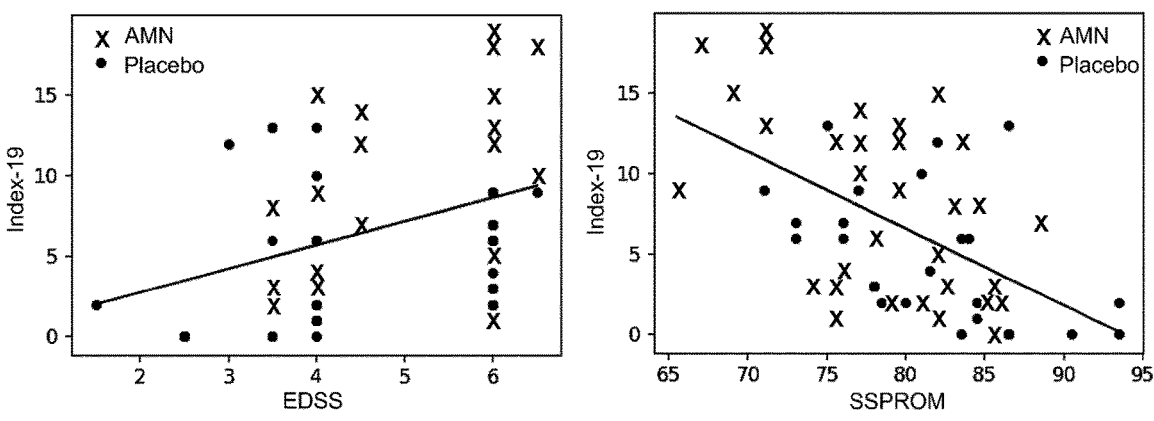

[Fig. 7]
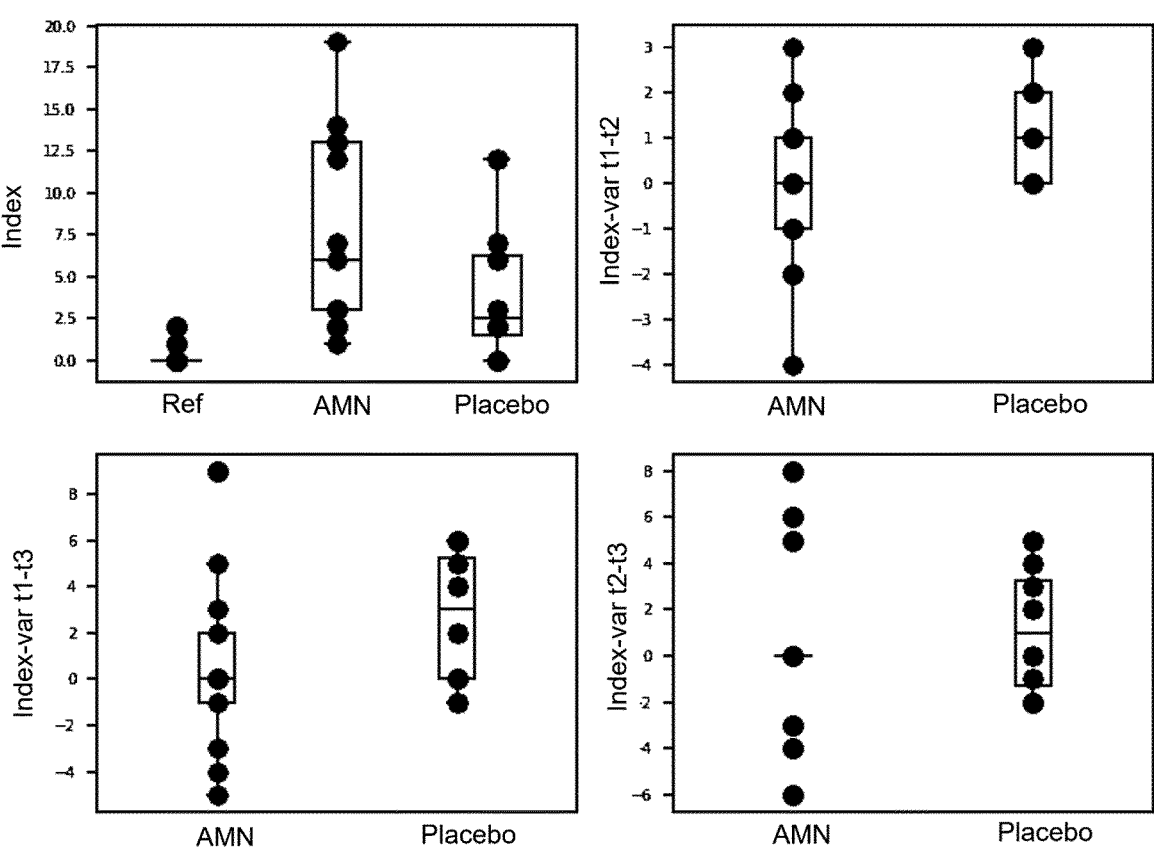

METHOD FOR DETERMINATION OF AN INDICATOR REPRESENTATIVE OF A CHANGE IN THE BRAIN OF AN INDIVIDUAL CAUSED BY A DEMYELINATING OR RELATED DISEASE, AFFECTING THE STATE OF THE MYELIN OF THE BRAIN

CROSS-REFERENCE TO RELATED APPLICATIONS

This application is the U.S. National Stage of PCT/EP2022/073240, filed Aug. 19, 2022, which in turn claims priority to French patent application number 2108808 filed Aug. 20, 2021. The content of these applications are incorporated herein by reference in their entireties.

TECHNICAL FIELD OF THE INVENTION

The technical field of the invention is that of magnetic resonance imaging (MRI) and more particularly diffusion tensor MRI for evaluating the degree of brain alteration of an individual suffering from a demyelinating or related pathology.

The present invention relates especially to a method for determining an indicator representative of a brain alteration of an individual caused by a demyelinating pathology. The invention also relates to a system for implementing this determination method.

TECHNOLOGICAL BACKGROUND OF THE INVENTION

Demyelinating pathologies include multiple sclerosis (MS), leukodystrophies and adrenomyeloneuropathy (AMN). This type of pathology is known as primary demyelination. The most common, MS, affects almost 3 million people worldwide.

Multiple sclerosis (MS) is an inflammatory autoimmune disease which causes axonal degeneration through an attack on the myelin sheath by the immune system. Although the causes of this disease are still uncertain, some factors, such as the combination of several genetic alternatives, the environment or an infection, appear to be risk factors for the development of this disease. The symptoms of MS are very varied: motor, sensory, visual, balance, urinary, sexual or cognitive disorders, and are all the direct consequence of demyelination of the nervous system.

Adrenomyeloneuropathy (AMN) is the most common peroxisomal disorder. It is caused by pathogenic ABCD1 variants on the X chromosome, which result in altered peroxisomal beta-oxidation and accumulation of very long-chain fatty acids in plasma and tissues, especially in the white matter of the brain, spinal cord and adrenal cortex, leading to demyelination of the nervous system. AMN results in clinically heterogeneous phenotypes, the most common of which is a disabling myeloneuropathy characterised by progressive spastic paraparesis with bladder troubles, sensory ataxia and leg pain.

There are other pathologies which result in the demyelination of axons. This is the case, for example, with amyotrophic lateral sclerosis (ALS). These diseases are categorised as secondary demyelination.

Amyotrophic lateral sclerosis (ALS) is a degenerative disease affecting motor neurons, the causes and mechanisms of which are still misunderstood. The first symptoms of this disease are mainly motor disorders affecting the arms, hands, legs or mouth, depending on the zones in the brain first affected, with difficulties in hinging or swallowing. As the disease progresses, the troubles spread to the muscles of the rest of the body, leading to muscle loss and coordination problems, even affecting the respiratory muscles. Some forms of ALS have also been found to cause cognitive problems. As in MS and AMN, ALS results in demyelination of axons, associated with the death of motor neurons.

These types of disease with primary or secondary demyelination, which are often very disabling, affect many people, and there is an urgent need for treatments that are more effective than current therapies. For MS and AMN, there are only treatments aimed at slowing down progression and preventing degenerative flare-up. For example, in the case of AMN, current treatments are symptomatic: haematopoietic stem cell grafting, which is performed to stop demyelinating and inflammatory lesions, does not appear to prevent progression of myelopathy in AMN.

In order to effectively evaluate lesions resulting from these pathologies and the effects of potential treatments (to enable the development and validation of new treatments), there is a real need for biomarkers, with high effect sizes, representative of a degree of brain alteration related to a progressive demyelinating pathology.

For these conditions, the severity of white matter lesions and their worsening are difficult to evaluate using the usual examination methods: for example, biomarkers provided by conventional magnetic resonance imaging (MRI) are not sufficiently robust because they often lead to the detection of false-positive results in healthy patients or false-negative results in patients with demyelinating pathologies.

Among brain MRI techniques, document WO2014060695A2 is also known. This describes a method for determining the probability of a patient coming out of a coma. For this, regional values of radial diffusion, axial diffusion and anisotropy fraction are determined for different regions of the brain. All of these values, normalised beforehand, are input to a classifier, which outputs a probability of coming out of coma. This classifier is trained beforehand on the basis of MRI images corresponding to healthy patients as well as patients with the disease (around a hundred patients in all, monitored over more than a year). However, the classifier described in this document is parameterised to determine a probability of coming out of coma, and not to detect or monitor evolution of a demyelinating disease as mentioned above (in other words, the values of adjustable parameters of the classifier, provided in this document, are adapted to determine the probability of coming out of coma, but a priori not to detect one of the diseases in question). Furthermore, the use of such a classifier is restrictive, due to the learning phase in question, which requires follow-up of numerous reference patients, serving only for this learning.

The invention described in document WO2014060695A2 instructs the use of biomarkers with high effect sizes that are robust and representative of brain lesions that have caused the coma state. In this case, these biomarkers are radial diffusion, axial diffusion and anisotropy fraction.

However, the method described in WO2014060695A2 relies on learning tools to predict the probability of coming out of coma state. These tools require a time-consuming learning phase that is not compatible with the need for rapid evaluation of the degree of brain alteration in a patient subject to AMN.

Thus, there is a need for biomarkers representative of the degree of brain alteration related to AMN, with high effect sizes, which are robust, quick to obtain, concise and easy to understand for a healthcare professional.

SUMMARY OF THE INVENTION

The invention offers a solution to the problems previously discussed, by allowing simple and rapid determination of a robust indicator representative of a degree of brain alteration caused by a demyelinating pathology in such a way that said indicator is concise and easy to understand for a health professional.

Demyelinating pathologies are considered to be all pathologies leading to primary demyelination, such as multiple sclerosis (MS), leukodystrophies or adrenomyeloneuropathy (AMN), or secondary demyelination, such as amyotrophic lateral sclerosis (ALS).

More precisely, the object of the present invention is a method, and a system for implementing the method, for determining said indicator.

A first aspect of the invention relates to a method for determining an indicator, representative of a brain alteration of an individual caused by a demyelinating pathology, comprising the following steps:

A first step, for each region of interest of a set gathering several regions of interest of the brain, of determining of a regional diffusion coefficient corresponding to an average, over said region of interest, of one of the following diffusion coefficients: radial diffusion, axial diffusion, mean diffusion, anisotropy fraction or a combination of several of these coefficients, the regional coefficients respectively associated with these different regions being determined from an image of the brain of the individual to be examined previously obtained by diffusion MRI;

A second step of determining a number of altered regions, by counting the number of regions of interest for which a given condition is satisfied, said condition relating to the value of the regional diffusion coefficient associated with the region under consideration, compared with a reference regional coefficient which is equal to an average of the regional diffusion coefficient for this region for a cohort of healthy patients;

A third step of determining said indicator as a function of the number of altered regions.

By virtue of the invention, a healthcare professional has an indicator representative of the brain alteration caused by a demyelinating pathology, and in particular representative of an alteration of the myelin. Indeed, diffusion coefficients obtained from MRI images of the diffusion tensor, such as radial diffusion, axial diffusion, mean diffusion, anisotropy fraction or a combination of several of these coefficients, are sensitive to myelin alterations. In addition, the indicator is determined for several regions of interest, making it representative of brain alteration at the individual's level. Furthermore, the indicator is representative of the alteration state of the brain because it is determined from averaged diffusion coefficients and is therefore of low sensitivity to measurement uncertainties and variabilities.

The indicator is also simple, concise, quantitative and easy to understand for the healthcare professional, since it is advantageously determined as a function of the number of altered regions of interest.

The indicator also enables the healthcare professional to evaluate the degree of severity of the alterations, especially by comparison with diffusion coefficients extracted from images acquired for the cohort of healthy patients.

The indicator is additionally representative of the evolution of the brain alteration and enables the healthcare professional to evaluate a change in the alteration over time and space, especially as the diseases concerned are distinguishable from other myelopathic disorders, especially because of their degenerative nature.

Lastly, the indicator represents the alteration state of the brain in that it is correlated with other indicators such as the EDSS (Expanded Disability Status Scale), which makes it possible to evaluate disability on a severity scale, and the SSPROM (Severity Score System for Progressive Myelopathy), which makes it possible to evaluate severity of affliction based on symptoms associated with myelopathy, such as motor disorders, sphincter dysfunction, spasticity and sensory alteration.

Further to the characteristics just discussed in the previous paragraphs, the method according to the first aspect of the invention may have one or more additional characteristics from among the following, considered individually or according to any technically possible combinations.

A first alternative embodiment relates to the method according to the invention wherein said indicator represents an evolutionary nature of said alteration, and wherein:

the image of the brain of the individual used in the first step is an image taken by diffusion MRI at a date t2, the method further including a step: for each of said regions of interest, of determining an initial regional coefficient corresponding to an average of the diffusion coefficient over the region of interest, said initial regional coefficients being determined from an initial image of the individual's brain, taken by diffusion MRI at a date t1 prior to date t2, in the second step, the number of altered regions corresponds to the number of regions with progression of the alteration, a region of interest being considered as a region with progression of the alteration when the condition is defined as follows: the regional diffusion coefficient has moved away from the reference regional coefficient, relative to the initial regional coefficient.

For each region of interest, it can be considered, for example, that the regional diffusion coefficient has moved away from the regional reference coefficient when the distance between the value of said regional coefficient, corresponding to t2, and the value of the regional reference coefficient is greater than the distance between the value of the initial regional coefficient, corresponding to t1, and the value of the regional reference coefficient.

By virtue of this alternative embodiment, it is possible to determine the progression of demyelination of the brain for each region of interest by comparing the initial regional coefficient obtained at a first date t1 with the regional coefficient obtained at a second date t2, and by comparing the regional coefficient with the reference coefficient obtained from the cohort of healthy patents. The method thus makes it possible to detect whether the alteration of an altered region of interest has degraded and whether an unaltered region of interest has become altered. The indicator determined by the method therefore represents the degenerative nature of a demyelinating pathology, even in the case of severe affliction.

The indicator is furthermore simple and concise since it expresses on its own whether there is an evolution in the brain alteration and whether the evolution is caused by a progression of the alteration.

A sub-alternative to the first alternative embodiment relates to the method according to the invention, wherein, in the second step, the regional diffusion coefficient has moved away from the reference regional coefficient, with respect to the initial regional coefficient when a distance between the regional coefficient and the initial regional coefficient is greater than $z_e \cdot \sigma_j$, wherein $\sigma_j$ represents a dispersion of said regional diffusion coefficient, for the region under consideration, for said cohort of healthy patients, and wherein $z_e$ is a minimum evolution coefficient, between 0.5 and 4.

By virtue of this sub-alternative, the brain regions are counted by the indicator only if the progression of their alteration is significant, i.e. if the evolution in their regional coefficient is greater than a value representative of a dispersion of said regional coefficient obtained for the cohort of healthy patients.

An alternative to the first alternative embodiment relates to the method of the invention, wherein said indicator represents an evolutionary nature of said alteration, and wherein said indicator is representative of an evolutionary nature of said alteration, and wherein in the second step the number of altered regions is the number of regions with regression of the alteration, a region of interest being considered as a region with regression of the alteration when said condition is that the regional diffusion coefficient has moved closer to the reference regional coefficient, with respect to the initial regional coefficient.

For each region of interest, for example, the regional diffusion coefficient may be considered to have moved closer to the regional reference coefficient when the distance between the value of said regional coefficient, corresponding to t2, and the value of the regional reference coefficient is smaller than the distance between the value of the initial regional coefficient, corresponding to t1, and the value of the regional reference coefficient.

A sub-alternative to the previous alternative embodiment relates to the method according to the invention, wherein said indicator is representative of an evolutionary nature of said alteration, and wherein, in the second step, the diffusion regional coefficient has moved closer to the reference regional coefficient, with respect to the initial regional coefficient when a distance between the regional coefficient and the initial regional coefficient is greater than $z_e \cdot \sigma_j$, where $\sigma_j$ is representative of a dispersion of said regional diffusion coefficient, for the region under consideration, for said cohort of healthy patients, and where $z_e$ is a minimum evolution coefficient, between 0.5 and 4.

By virtue of this sub-alternative, it is possible to determine regression of brain demyelination for each region of interest by comparing the initial regional coefficient obtained at a first date with the regional coefficient obtained at a second date, and by comparing the regional coefficient with the reference coefficient obtained from the cohort of healthy patients. The method thus makes it possible to detect whether the alteration of an altered region of interest has improved and whether an altered region of interest has become non-altered. Furthermore, the brain regions are counted by the indicator only if the regression of their alteration is significant, i.e. if the evolution in their regional coefficient is greater than the value representative of a dispersion of said regional coefficient obtained for the cohort of healthy patients.

The indicator determined by the method then expresses whether there is an evolution of the brain alteration and whether the evolution is caused by a regression of the alteration.

A sub-alternative embodiment compatible with the previous sub-alternative embodiments relates to the method of the invention wherein the indicator representative of an evolutionary nature of said alteration is all the greater as a difference between the number of regions with progression of the alteration and the number of regions with regression of the alteration is great.

The indicator is therefore easy for the healthcare professional to understand since it is simple, concise, quantitative and representative of the brain alteration caused by a demyelinating pathology.

An alternative embodiment relates to the method according to the invention for which the date t2 is subsequent to a date of administration of a treatment for brain alteration related to a demyelinating pathology type of affliction, and the date t1 is prior to said date of administration of said treatment.

By virtue of this alternative, the indicator determined by the method makes it possible to evaluate evolution of the brain alteration after administration of a treatment against demyelination.

A second alternative embodiment describes the method according to the invention wherein said indicator is a static indicator of the level of brain affliction, and wherein, in the second step, said condition is that a distance between the regional diffusion coefficient and the regional reference coefficient is greater than $z_s \cdot \sigma_j$ where $\sigma_j$ is representative of a dispersion of said regional diffusion coefficient, for the region under consideration, for said cohort of healthy patients, and where $z_s$ is a minimum distance coefficient, between 0.5 and 4.

This second alternative makes it possible to obtain an indicator representative of the alteration state of the brain at a given moment and which provides information on the degree of severity of demyelination of the brain at the individual's level.

This static indicator is furthermore simple, concise, quantitative and easy for the healthcare professional to understand, since it is a single scalar expressing the number of regions of interest whose alteration is significant compared with a cohort of healthy patients.

An alternative embodiment of the method according to the invention describes that the plurality of regions of interest is chosen from all or some of the following regions: anterior brainstem, anterior brainstem, right peduncle, left peduncle, genu of the corpus callosum, trunk of the corpus callosum, splenium of the corpus callosum, anterior limb of the right internal capsule, anterior limb of the left internal capsule, posterior limb of the right internal capsule, posterior limb of the left internal capsule, right sagittal stratum, left sagittal stratum, right superior longitudinal fasciculus, left superior longitudinal fasciculus, right external capsule, left external capsule, right corona radiata and left corona radiata.

An alternative embodiment relates to the method according to the invention in that the cohort of healthy individuals comprises at least two healthy individuals for each region of interest.

An alternative embodiment describes the method according to the invention in that at least one of the at least two healthy individuals is the same or is different for each region of interest.

In other words, for each region of interest, the regional reference coefficient may be determined from the same cohort of healthy individuals or from a different cohort of healthy individuals.

A second aspect of the invention relates to a system for implementing the method according to any of the preceding embodiments, including a processing module configured to perform the following steps:

A first step, for each region of interest of a set gathering several regions of interest of the brain, of determining a regional diffusion coefficient corresponding to an average, over said region of interest, of one of the following diffusion coefficients: radial diffusion, axial diffusion, mean diffusion, anisotropy fraction or a combination of several of these coefficients, the regional coefficients respectively associated with these different regions being determined from an image of the brain of the individual to be examined previously obtained by diffusion MRI;

A second step of determining a number of altered regions, by counting the number of regions of interest for which a given condition is satisfied, said condition relating to the value of the regional diffusion coefficient associated with the region under consideration, relative to a reference regional coefficient which is equal to an average of the regional diffusion coefficient for this region for a cohort of healthy patients;

A third step of determining said indicator as a function of the number of altered regions.

A final aspect of the invention relates to a computer program product comprising instructions which, when the program is executed by a computer, cause the same to implement the steps of the method according to any of the preceding embodiments.

The invention and its different applications will be better understood upon reading the following description and upon examining the accompanying figures.

BRIEF DESCRIPTION OF THE FIGURES

The figures are set forth by way of indicating and in no way limiting purposes of the invention.

FIG. 1 illustrates an embodiment of the system according to the invention.

FIG. 2 is a general description of the method according to the invention.

FIG. 3 is a block diagram illustrating a first embodiment of the method according to the invention.

FIG. 4 is a block diagram illustrating a second embodiment of the method according to the invention.

FIG. 5 illustrates a second embodiment of the system according to the invention.

FIG. 6 compares experimental results of the indicator, determined by the second embodiment of the method of FIG. 4 for a plurality of individuals suffering from adrenomyeloneuropathy, with the EDSS and SSPROM indicators.

FIG. 7 gathers experimental results of the indicator determined by the two embodiments of the method of FIGS. 3 and 4 for a plurality of individuals suffering from adrenomyeloneuropathy.

DETAILED DESCRIPTION

Unless otherwise specified, a same element appearing in different figures has a single reference.

The present invention relates to a system and a method implemented by the system. The method is utilised to determine an indicator which is representative of a brain alteration of an individual caused by demyelination of the nervous system due to a pathology resulting in primary or secondary primary demyelination. The system, which includes three distinct sub-systems, is described referring to FIG. 1. The method of the invention is then described in detail, from FIGS. 2 and 3. Two alternatives to the method are provided, one making it possible to determine the alteration to the myelin sheath at a given time, and the other making it possible to monitor evolution of demyelination in the brain over time. This method is based on diffusion coefficients calculated from anisotropic variations in the magnetic field measured by MRI of the diffusion tensor of a patient's brain, and compares these coefficients with data from a cohort of healthy patients.

Disclosure of the System

A first aspect of the invention relates to a system for determining a brain alteration of an individual caused by a demyelinating pathology.

FIG. 1 shows a schematic representation of the system 10 according to the invention.

The system 10 comprises:

An acquisition system 20, comprising:
    a control module 21; and
    a diffusion tensor MRI (Magnetic Resonance Imaging) imaging module 22;

A processing system 30, comprising:
    A volatile memory 31;
    A processing module 32;
    A non-volatile memory 33;

An information system 40, comprising:
    A display module 41

A connection 50 connecting the acquisition system 20 and the processing system 30;

A connection 60 connecting the acquisition system 20 and the information system 40;

A connection 70 connecting the processing system 30 and the information system 40.

The acquisition system 20 is configured to carry out acquisition of diffusion tensor MRI images of the brain for an individual. More precisely, the control module 21 is configured to drive the imaging module 22 so as to carry out diffusion tensor MRI acquisition of an image of the individual's brain, and to acquire this image.

By diffusion tensor MRI, it is meant any technique for measuring by MRI the distribution of diffusion directions of water molecules which is sensitive to the anisotropy of the fibrous structure of the brain.

The control module 21 may be a computer, a mobile apparatus, a processor, or any other apparatus capable of executing instructions to drive the imaging module 22 and thus to acquire and store in memory the diffusion tensor MRI image of the brain.

The imaging module may, for example, be a 1.5 Tesla, 3.0 Tesla or 7.0 Tesla MRI apparatus, for example from the company Philips™, General Electric™ (GE) or Siemens™.

The image of the brain can be any type of image obtained by an MRI apparatus. For example, it may be a non-weighted image or a diffusion-weighted image.

The control module 21 may be controlled by a practitioner performing the imaging or may be autonomous and follow pre-recorded instructions.

The acquisition system 20 is configured to transmit, via the connection 50, to the processing system 30 a piece of data relating to the acquired image of the brain, this piece of data being able, for example, to be all or part of the image of the brain or a piece of data obtained from the image of the brain after processing, for example after filtering, segmentation, averaging or classification.

The connection 50 between the acquisition system 20 and the processing system 30 may be wired (e.g. Ethernet, USB, SATA, PCI) or wireless (e.g. WiFi, Bluetooth) in character.

The processing system 30 is configured to receive the piece of data received by the processing system 30 via the connection 50 from the acquisition system 20.

The processing system 30 is further configured to process the piece of data.

The processing system 30 may be any system for executing instructions. For example, the processing system 30 may be a computer or a server. The processing system 30 may also be local or remote, for example in the form of a cloud-type service.

Disclosure of the Method

The processing system 30 is configured to implement a method according to the invention 100 as illustrated in FIG. 2. The method 100 allows determination of an indicator, representative of a brain alteration of an individual caused by a disease of the demyelinating pathology type, affecting the state of the myelin of the brain.

The method 100 comprises a step 101 during which, for each region of interest $ROI_j$ of a set gathering several regions of interest $ROI_1, \ldots ROI_j, \ldots ROI_N$ of the brain, a regional diffusion coefficient $C_j$ is determined. This regional coefficient $C_j$ corresponds to an average, over said region of interest $ROI_j$, of one of the following diffusion coefficients: radial diffusion, axial diffusion, mean diffusion, anisotropy fraction or a combination of several of these coefficients. The regional coefficients respectively associated with these different regions $ROI_1, \ldots ROI_j, \ldots ROI_N$ are determined from a image of the brain of the individual to be examined previously obtained by diffusion MRI. By "previously", it is meant that the image of the brain is acquired prior to implementing of the method described above, for example upon examining the individual. The method does not therefore require the presence of the individual in order to be implemented, only the image is necessary.

The regions of interest $ROI_1, \ldots ROI_j, \ldots ROI_N$ are brain regions, and in particular white matter regions, as defined by the ICBM-DTI-81 atlas with 48 white matter regions constructed from diffusion data of 81 healthy subjects (Mori et al. 2005). By healthy subjects, it is meant living beings with a brain, whether animal or human, with no brain disorder or affliction of any kind.

The regions of interest $ROI_1$, $ROI_j$, $ROI_N$ can be chosen from the following regions: anterior brainstem (ICBM 2, 7 and 8), posterior brainstem (ICBM 9 to 14), right cerebral peduncle (ICBM 15), left cerebral peduncle (ICBM 16), genu of the corpus callosum (ICBM 3), trunk of the corpus callosum (ICBM 4), splenium of the corpus callosum (ICBM 5), anterior limb of the right internal capsule (ICBM 17), anterior limb of the left internal capsule (ICBM 18), posterior limb of the right internal capsule (ICBM 19), posterior limb of the left internal capsule (ICBM 20), right sagittal stratum (ICBM 21, 29, 31 and 47), left sagittal stratum (ICBM 22, 30, 32 and 48), right superior longitudinal fasciculus (ICBM 41), left superior longitudinal fasciculus (ICBM 42), right external capsule (ICBM 33), left external capsule (ICBM 34), right corona radiata (ICBM 23, 25 and 27) and left corona radiata (ICBM 24, 26 and 28).

The notation "ICBM n" refers to the nth region of the ICBM-DTI-81 atlas.

It is possible to use other regions of the ICBM-DTI-81 atlas than those above mentioned, just as it is possible to arrange the regions differently so as to combine or split them differently from the arrangement provided by the ICBM-DTI-81 atlas.

It is also possible to use other atlases such as Schotten's Catani-Thiebaut atlas.

On the other hand, it is possible to rely on segmentation techniques to identify and delimit regions of interest in the image. For example, it is possible to apply segmentation by edge detection or shape recognition. It is further possible to rely on machine learning tools to identify the regions of interest.

Thus, for each of the regions of interest $ROI_1, \ldots ROI_j, \ldots ROI_N$, the regional diffusion coefficient $C_j$ is determined by the average of at least one diffusion coefficient of said region of interest $ROI_j$.

The average may be, but is not restricted to, a spatial average, calculated by taking the values of the diffusion coefficient measured on each voxel of the image of the brain. It may also be a weighted average, for example by the area of the region of interest $ROI_j$ or by a regularisation function.

The method 100 comprises a second step 102 of determining a number of altered regions Na, by counting the number of regions of interest $ROI_1, \ldots ROI_j, \ldots ROI_N$ for which a given condition is satisfied, said condition relating to the value of the regional diffusion coefficient $C_j$ associated with the region under consideration, compared with a reference regional coefficient $C_{j,ref}$ which is equal to an average of the regional diffusion coefficient for this region for a cohort of healthy patients.

For each region of interest $ROI_j$ of the brain, a regional reference coefficient $C_{j,ref}$ is determined. This regional reference coefficient $C_{j,ref}$ indicates a reference value for the diffusion coefficient concerned. This reference value indicates an average normal value for the diffusion coefficient for an individual not suffering from a demyelinating pathology. The regional reference coefficient $C_{j,ref}$ is obtained by averaging the values of the regional diffusion coefficient determined on a cohort of healthy patients. This average may possibly be weighted.

Determining the regional reference coefficients requires to have a cohort of patients available. At least two healthy patients per region of interest $ROI_j$ are required. It is additionally possible for the regional reference coefficients to be determined with a totally or partially different cohort of healthy patients for each region of interest $ROI_j$ in the brain. The challenge of such a cohort is to have a robust estimation of the regional reference coefficients.

A region of interest $ROI_j$ is therefore said to be altered when it fulfils said condition relating to the value of the regional coefficient $C_j$ and the value of the regional reference coefficient $C_{j,ref}$ of the region of interest concerned.

For each region of interest $ROI_j$, the regional coefficient $C_j$ may be pre-processed. For example, each regional coefficient $C_j$ may be normalised or made dimensionless by the reference regional coefficient $C_{j,ref}$ of said region of interest $ROI_j$, or centred and reduced by subtracting from it the mean of the regional coefficient values obtained from the cohort of healthy patients and then dividing by the standard deviation of the regional coefficient values obtained for the cohort of healthy patients.

The method 100 comprises a third step 103 of determining said indicator as a function of the number of altered regions Na.

Embodiment for Determining an Evolutionary Indicator

The method 100 may be implemented according to two complementary and independent embodiments. In a first embodiment, an indicator representative of the evolutionary nature of said alteration is obtained. In a second embodiment, a static indicator of the level of affliction to the brain is obtained. Thus, as will be appreciated by a person skilled in the art, these embodiments may be performed independently of one another or simultaneously, or may be combined or only partially performed.

FIG. 3 schematically illustrates the operation of the method 100, to which an additional step 201 is added, to determine the indicator representative of the evolutionary nature of the alteration.

In this first embodiment, the method 100 for determining the indicator representative of an evolutionary nature of the alteration repeats the three steps 101, 102 and 103 of the method 100 previously described, to which the following characteristics are joined:

the image of the individual's brain employed in the first step 101 is an image taken by diffusion MRI at a date t2, the method further including a step 201: for each of said regions of interest $ROI_1, \ldots ROI_j, \ldots ROI_N$, of determining an initial regional coefficient $C_{j,0}$, corresponding to an average of the diffusion coefficient over the region of interest $ROI_j$, said initial regional coefficients being determined from an initial image of the individual's brain, taken by diffusion MRI at a date t1 prior to the date t2, in the second step 102, the number of altered regions Na corresponds to the number of regions with progression Np of the alteration, a region of interest $ROI_j$ being considered as a region with progression of the alteration when the condition is defined as follows: the regional diffusion coefficient $C_j$ has moved away from the reference regional coefficient $C_{j,ref}$ with respect to the initial regional coefficient $C_{j,0}$.

In other words, a first diffusion tensor MRI image acquisition is carried out at a date t1 by the acquisition system 20. A second acquisition is then carried out at a date t2 subsequent to t1 by the acquisition system 20. The time interval between t1 and t2 depends on the examination context and may, for example, be one day, one month or one year.

The interest of having images of the brain at two more or less distant successive times available is to be able to evaluate evolution of myelin alteration. This may involve monitoring the progression or regression of the alteration through the natural evolution of the disease. It can also be used to monitor evolution of the alteration after administration of a treatment which has an effect on myelin. Method 100 can then be used to evaluate effectiveness of the treatment by evaluating the progression or regression of the brain alteration.

Images acquired on dates t1 and t2 are transmitted to the processing system 30 to perform the steps of method 100. Thus, the processing system executes the first step 101 of the method 100 which relates to the determination of regional coefficients for the image acquired at time t2, and executes step 201 of the method 100 which relates to the determination of initial regional coefficients for the image acquired at time t1.

The regional coefficients and the initial regional coefficients are then compared with the reference regional coefficients in order to ascertain whether, for each region of interest $ROI_j$, the value of the regional coefficient $C_j$ has moved away from or closer to the value of the reference regional coefficient $C_{j,ref}$ with respect to the value of the initial regional coefficient $C_{j,0}$.

The objective is to determine the regions of interest $ROI_1, \ldots ROI_N$ for which the evolution of the regional coefficient $C_j$ between instants t1 and t2 corresponds to a progression of the alteration and those for which the evolution corresponds to a regression of the alteration.

It is thereby possible to determine the indicator representative of an evolutionary nature of said alteration by counting the number of regions of interest $ROI_1, \ldots ROI_j, \ldots ROI_N$ for which the evolution corresponds to a progression or regression of the alteration. This count can also be weighted according to each region of interest $ROI_j$, for example according to their location or relevance to the disease or clinical examination.

For each region of interest $ROI_j$, it is further possible, in the second step 102, to evaluate whether the evolution of the alteration is significant by quantifying the distance between the initial regional coefficient $C_{j,0}$ and the regional coefficient $C_j$, in the event that the progression or regression of the brain alteration is proven. This distance is for example equal or proportional to the difference between the regional coefficient $C_j$ and the initial regional coefficient $C_{j,0}$.

To this end, it is possible, in the second step 102, to determine whether, for each region, the difference between the regional coefficient $C_j$ and the initial regional coefficient $C_{j,0}$ is greater than $z_e \cdot \sigma_j$, where:

$\sigma_j$ is for example the standard deviation of the values of the regional coefficient $C_j$ of the region of interest $ROI_j$ determined for the cohort of healthy patients, or of any other quantity representative of the dispersion of the values of the regional coefficient determined for the cohort of healthy patients for the region of interest $ROI_j$. $\sigma_j$ may possibly be different if the regions of interest $ROI_1, \ldots ROI_j, \ldots ROI_N$ are with progression of the alteration or regression of the alteration. $\sigma_j$ can possibly be different for each region of interest $ROI_j$;

$z_e$ is a minimum evolution coefficient, for example between 0.5 and 4, the purpose of which is to define a fraction of $\sigma_j$ above which it is considered that the evolution is significant. $z_e$ may possibly be different if the regions of interest $ROI_1, \ldots ROI_j, \ldots ROI_N$ are with progression of the alteration or regression of the alteration. $z_e$ can possibly be different for each region of interest $ROI_j$.

For example, it is possible to define that the evolution of the alteration is significant in the region of interest $ROI_j$ when the distance between the regional coefficient $C_j$ and the initial regional coefficient $C_{j,0}$ is greater than one times the standard deviation calculated from the values of the regional coefficient obtained for the cohort of healthy patients.

It is thereby possible, in the third step 103, to determine the indicator representative of an evolutionary nature of said alteration as being equal or proportional to the number of regions of interest $ROI_1, \ldots ROI_j, \ldots ROI_N$ for which the evolution corresponds to a progression or regression of the alteration and for which the progression or regression of the alteration is significant.

Furthermore, it is contemplatable that the indicator representative of an evolutionary nature of said alteration, determined in the third step 103, is determined by calculating a distance, proportional to a difference, between the number of regions of interest $ROI_1, \ldots ROI_j, \ldots ROI_N$ for which there is a proven and significant progression of the alteration and those for which there is a proven and significant regression of the alteration.

Furthermore, if date t1 is prior to the administration of a treatment and the date t2 is subsequent to the administration of said treatment, the indicator is also representative of the effect of said treatment on evolution of the brain alteration.

Embodiment for Determining a Static Indicator

In the second embodiment, the indicator determined by the method 300 is a static indicator of the level of brain affliction.

FIG. 4 schematically illustrates the operation of the method 100 according to the second embodiment.

In this first embodiment, the method 100 for determining the static indicator of level of brain affliction repeats the three steps 101, 102 and 103 of the method 100 previously described. The method has the following characteristic joined thereto: in the second step 102, said condition is that a distance between the regional diffusion coefficient $C_j$ and the regional reference coefficient $C_{j,ref}$ is greater than $z_s \cdot \tau_j$. $\tau_j$ is representative of a dispersion of said regional diffusion coefficient, for the region under consideration, for said cohort of healthy patients, and $z_s$ is a minimum distance coefficient of between 0.5 and 4.

The static indicator makes it possible to determine, from the image of the brain, the level of brain affliction at a given time.

In other words, for each region of interest $ROI_j$, the distance between the regional coefficient $C_j$ and the reference regional coefficient $C_{j,ref}$ is determined. This distance is, for example, equal to or proportional to the difference between the regional coefficient $C_j$ and the regional reference coefficient $C_{j,ref}$.

It is thereby possible to evaluate whether the alteration is significant by determining, for each region $ROI_j$, whether said distance is greater than $z_s \cdot \tau_j$. where:

$\tau_j$ is for example the standard deviation of the values of the regional coefficient of the region of interest $ROI_j$ determined for the cohort of healthy patients, or of any other quantity representative of the dispersion of the values of the regional coefficient determined for the cohort of healthy patients for the region of interest $ROI_j$. $\tau_j$ may be different for each region of interest $ROI_j$; $\tau_j$ may possibly be equal to $\sigma_j$;

$z_s$ is a minimum distance coefficient, for example between 0.5 and 4, the purpose of which is to define a fraction of $\tau_j$ above which the alteration is considered significant. $z_s$ may possibly be different for each region of interest $ROI_j$.

For example, it is possible to define that the alteration is significant in the region of interest $ROI_j$ when the distance between the regional coefficient $C_j$ and the reference regional coefficient $C_{j,ref}$ is greater than twice the standard deviation calculated from the values of the regional coefficient obtained for the cohort of healthy patients.

It is thereby possible to determine the static indicator of the level of brain affliction as being equal or proportional to the number of regions of interest $ROI_1, \ldots ROI_j, \ldots ROI_N$ for which the alteration is significant.

Disclosure of the Display System

The display system is configured to receive from the processing system 30, via the connection 70, the indicator representative of a brain alteration of an individual caused by a disease of the demyelinating pathology type affecting the state of the myelin of the brain. This indicator can be determined according to one of the two embodiments described earlier.

The display system 40 is further configured to allow a healthcare professional to receive the indicator determined by the method 100.

The connection 70 may be wired (for example: Ethernet, USB, SATA, PCI) or non-wired (for example: Wifi, Bluetooth) in character.

The display system 40 may also be configured so as to receive from the acquisition system 20, via the connection 60, a piece of data relating to the acquired image of the brain, which may be a piece of data different from that transmitted from the acquisition system 20 to the processing system 30 via the connection 50.

The connection 60 may be wired (e.g. Ethernet, USB, SATA, PCI) or wireless (e.g. WiFi, Bluetooth) in character.

The healthcare professional can then have access to the piece of data resulting from the acquisition, for example the image of the brain, and to the result of the method 100.

The acquisition system 20 can therefore also be configured to transmit the acquisition piece of data to the display system 40.

The acquisition system 40 may therefore be configured to display the acquisition piece of data transmitted by the acquisition system 20.

The display module 41, which enables the system to receive and display the indicator of the method 100 and possibly the acquisition piece of data, may be any apparatus capable of receiving and displaying a piece of data (for example a tablet, a mobile phone, a laptop or desktop computer, a connected object, etc.).

The display system 40 may possibly be intended for the patient so that he can have access to results of his examination, for example to receive the indicator of the method 100 and possibly the image of his brain.

Alternatively, the display module 41 may be an information module that provides a piece of information relating to the indicator of the method 100. For example, the information module may orally inform the patient who accesses the display system 40 to receive their indicator of the method 100, in the event that this patient is visually altered. In another example, the information module may display a comment relating to the brain alteration and not display the indicator of the method 100 as such. By these examples, the person skilled in the art will be able to understand that the display module 41 can inform the patient or the healthcare professional wishing to access the indicator of the method 100 in several ways.

System for Imaging a Cohort of Healthy Patients

The method 100 is based on the availability of regional reference coefficients obtained from a cohort of healthy individuals.

Thus, FIG. 5 illustrates a system for obtaining regional reference coefficients from a cohort of healthy individuals.

The system 80 includes:

A control module 81; and

A diffusion tensor MRI imaging module 82.

The acquisition system 80 is configured to acquire diffusion tensor MRI images of the brain for the cohort of healthy patients. More precisely, the control module 81 is configured to drive the imaging module 82 so as to perform diffusion tensor MRI acquisition of an image of the brain of each individual of the cohort of healthy patients, and to acquire this image.

By diffusion tensor MRI, it is meant any technique for measuring by MRI the distribution of diffusion directions of water molecules which is sensitive to the anisotropy of the fibrous structure of the brain.

The control module 81 may be a computer, a mobile apparatus, a processor, or any other apparatus capable of executing instructions to drive the imaging module 82 thus acquiring and storing in memory the diffusion tensor MRI image of the brain.

The imaging module may, for example, be a 1.5 Tesla, 3.0 Tesla or 7.0 Tesla MRI apparatus, for example from the company Philips, General Electric (GE) or Siemens.

The image of the brain is preferably a diffusion weighted image.

The control module 81 may be controlled by a practitioner performing the imaging or may be autonomous and follow pre-recorded instructions.

The control module 81 may be the same as or different from that used by the system 20.

Similarly, the imaging module 82 may be identical to or different from that used by the system 20.

It is possible that, once all the brain images of the cohort of healthy patients have been acquired, the control module 81 determines for each region of interest $ROI_j$ the reference regional coefficient from the brain images collected from the cohort of healthy patients.

It is also possible for the determination of the reference regional coefficients to be carried out by the processing module 30 or by another module external to the systems 10 and 80.

For each region of interest $ROI_j$, the value of the reference regional coefficient $C_{j,ref}$ may be equal or proportional to an average of the values of the regional coefficients obtained for each individual of the cohort of healthy patients for said region $ROI_j$. This average may be performed differently depending on the region of interest $ROI_j$ under consideration.

Once determined, it is contemplatable that the reference regional coefficients are stored in memory in one of the systems 20, 30, 40 or 80, or another system external to the systems 10 and 80. If the regional coefficients are stored on the processing system 30, they may be stored in the non-volatile memory 31 or in the volatile memory 33. If the regional coefficients are stored on the acquisition system 20 or the display system 40, the processing system 30 can access these coefficients via one of the connections 50 or 70. If these coefficients are stored on the acquisition system 80 or a system other than systems 10 and 80, these coefficients are accessible to the processing system 30 via a wired or non-wired connection.

By wired connection, it is meant a hardware connection between two systems or modules, for example an Ethernet, USB, PCI or SATA connection. A non-wired connection is understood to be a non-hardware connection between two systems or modules, for example a WiFi or Bluetooth connection.

Application Example

An application example of the method 100 is provided below.

The purpose of this study is to highlight the effect of a treatment on brain demyelination.

For this example, the method is applied to a cohort of patients suffering from adrenomyeloneuropathy (AMN). This cohort is then split into two groups: the AMN group, which will receive the treatment, and the placebo group, which will receive a placebo of the treatment.

This example only deals with regional coefficients determined from regional radial diffusion values.

On the one hand, the reference regional coefficients are determined from a cohort of healthy patients, thus defined by the above method.

The regions of interest $ROI_1, \ldots ROI_j, \ldots ROI_N$ of the brain considered are 19 in number and are: anterior brainstem (ICBM 2, 7 and 8), posterior brainstem (ICBM 9 to 14), right cerebral peduncle (ICBM 15), left cerebral peduncle (ICBM 16), genu of the corpus callosum (ICBM 3), trunk of the corpus callosum (ICBM 4), splenium of the corpus callosum (ICBM 5), anterior limb of the right internal capsule (ICBM 17), anterior limb of the left internal capsule (ICBM 18), posterior limb of the right internal capsule (ICBM 19), posterior limb of the left internal capsule (ICBM 20), right sagittal stratum (ICBM 21, 29, 31 and 47), left sagittal stratum (ICBM 22, 30, 32 and 48), right superior longitudinal fasciculus (ICBM 41), left superior longitudinal fasciculus (ICBM 42), right external capsule (ICBM 33), left external capsule (ICBM 34), right corona radiata (ICBM 23, 25 and 27) and left corona radiata (ICBM 24, 26 and 28).

In addition, for each region of interest $ROI_j$ for a cohort of AMN patients, a regional coefficient $C_j$ is determined. The AMN group and the placebo group are treated separately.

These regional coefficients are reduced and centred with the average and standard deviation of the values of the reference regional coefficient $C_{j,ref}$ for each region. Thus each regional coefficient $C_j$ is expressed as a fraction of the standard deviation of the values of the regional reference coefficient $C_{j,ref}$ for the region under consideration.

Firstly the static indicator is determined, for each patient suffering from AMN, on the basis of these 19 regions of interest $ROI_1, \ldots ROI_j, \ldots ROI_N$. In other words, the number of altered regions of interest is counted. Altered regions of interest are those where the difference between the centred reduced regional coefficient $C_j$ and the zero value is greater than twice the standard deviation of the values of the reference regional coefficient $C_{j,ref}$. The static indicator is then the total number of altered regions of interest. This indicator is hereafter called "index-19".

Secondly, the evolution indicator is determined.

The regional coefficients obtained for index-19 become the initial regional coefficients.

At a date subsequent to the acquisition of images to determine the index-19, which corresponds to date t2 of the method, a new acquisition of images is carried out for each patient in the cohort of patients with AMN. Regional coefficients are extracted from these images. These regional coefficients are also centred and reduced with the average and standard deviation of the values of the reference regional coefficient $C_{j,ref}$ for each region.

The date t2 is subsequent to the administration of a treatment for the AMN group and of a placebo of this treatment for the placebo group.

The regional coefficients are compared to the initial regional coefficients to identify the regions for which there is an evolution of the alteration.

It is thereby possible to determine the regions for which there is a progression of the alteration, i.e. the regions where the value of the regional coefficient $C_j$ has moved away from the reference regional coefficient $C_{j,ref}$ (herein of zero value) from the initial regional coefficient $C_{j,0}$.

It is also possible to determine the regions for which there is a regression of the alteration, i.e. the regions where the value of the regional coefficient $C_j$ has moved closer to the regional reference coefficient $C_{j,ref}$ (herein of zero value) from the initial regional coefficient $C_{j,0}$.

Quantifying the difference between the value of the regional coefficient $C_j$ and that of the initial regional coefficient $C_{j,0}$, for each region of interest $ROI_j$, makes it possible to identify regions for which evolution of the alteration is significant. Herein, the evolution is considered significant when the difference between the two values is greater than one times the standard deviation of the values of the reference regional coefficient $C_{j,ref}$ for each region of interest $ROI_j$.

The evolution indicator is then determined as a function of the number of regions of interest $ROI_1, \ldots ROI_j, \ldots ROI_N$ for which there is progression of the alteration and the number of regions of interest $ROI_1, \ldots ROI_j, \ldots ROI_N$ for which there is regression of the alteration. The evolution indicator here is the difference between these two numbers. The evolution indicator is then called "index-var t1-t2".

In a third step, the method is repeated for a date t3 subsequent to t2. The index-var t1-t3, which expresses the evolution of brain alteration between date t1 and date t3, and the index-var t2-t3, which expresses the evolution of brain alteration between date t2 and date t3, are then determined.

FIG. 5 shows the index-19 as a function of the EDSS and SSPROM scores mentioned above. The figure shows the correlation between the EDFF and SSPROM indicators for the AMN and placebo groups. The black line indicates the regression curve between the respective indicators for all patients.

FIG. 6 shows the distribution of index-19 values for the cohort of healthy patients (here indicated by the Ref group) and for the AMN and placebo groups. The index-var t1-t2, index-var t1-t3 and index-var t2-t3 for the AMN and placebo groups are also shown. The figure shows the significant differences in index and index-var values between the different groups. In particular, after administration of the treatment, the evolution of the alteration is much less significant in the AMN group than in the placebo group. This implies both that the treatment has an effect on demyelination and that the biomarker used here, herein radial diffusion, is sensitive to the state of myelin alteration. This sensitivity is further noticeable by the static indicator, where the distribution of index values shows a sharp difference between healthy and AMN patients.

The invention claimed is:

1. A method for determining an indicator, representative of a brain alteration of an individual caused by a demyelinating pathology, the method comprising:
   a first step, for each region of interest of a set gathering several regions of interest of the brain, of determining a regional diffusion coefficient corresponding to an average, over said region of interest, of one of the following diffusion coefficients: radial diffusion, axial diffusion, mean diffusion, anisotropy fraction or a combination of several of these coefficients, the regional coefficients respectively associated with these different regions being determined from an image of the brain of the individual to be examined previously obtained by diffusion MRI;
   a second step of determining a number of altered regions, by counting the number of regions of interest for which a given condition is satisfied, said condition relating to the value of the regional diffusion coefficient associated with the region under consideration, compared with a reference regional coefficient which is equal to an average of the regional diffusion coefficient for this region for a cohort of healthy patients; and
   a third step of determining said indicator as a function of the number of altered regions.

2. The method according to claim 1, wherein said indicator is representative of an evolutionary nature of said alteration, and wherein:
   the image of the brain of the individual used in the first step is an image taken by diffusion MRI at a date t2,
   the method further including a step: for each of said regions of interest, of determining an initial regional coefficient corresponding to an average of the diffusion coefficient over the region of interest, said initial regional coefficients being determined from an initial image of the individual's brain, taken by diffusion MRI at a date t1 prior to the date t2,
   in the second step, the number of altered regions corresponds to the number of regions with progression of the alteration, a region of interest being considered as a region with progression of the alteration when the condition is defined as follows: the regional diffusion coefficient has moved away from the reference regional coefficient, relative to the initial regional coefficient.

3. The method according to claim 1, wherein said indicator is a static indicator of the level of brain affliction, and wherein, in the second step, said condition is that a distance between the regional diffusion coefficient and the regional reference coefficient is greater than $z_s \cdot \tau_j$ where $\tau_j$ is representative of a dispersion of said regional diffusion coefficient, for the region under consideration, for said cohort of healthy patients, and where $z_s$ is a minimum distance coefficient of between 0.5 and 4.

4. The method according to claim 1, characterised in that wherein the plurality of regions of interest is selected from all or some of the following regions: anterior brainstem, posterior brainstem, right cerebral peduncle, left cerebral peduncle, genu of the corpus callosum, trunk of the corpus callosum, splenium of the corpus callosum, anterior limb of the right internal capsule, anterior limb of the left internal capsule, posterior limb of the right internal capsule, posterior limb of the left internal capsule, right sagittal stratum, left sagittal stratum, right superior longitudinal fasciculus, left superior longitudinal fasciculus, right external capsule, left external capsule, right corona radiata and left corona radiata.

5. The method according to claim 1, wherein the cohort of healthy individuals comprises at least two healthy individuals for each region of interest.

6. A system for implementing a method according to claim 1, comprising:
   a processing module configured to perform the following steps:
      a first step, for each region of interest of a set gathering several regions of interest of the brain, of determining a regional diffusion coefficient corresponding to an average, over said region of interest, of one of the following diffusion coefficients: radial diffusion, axial diffusion, mean diffusion, anisotropy fraction or a combination of several of these coefficients, the regional coefficients respectively associated with these different regions being determined from an image of the brain of the individual to be examined previously obtained by diffusion MRI;
      a second step of determining a number of altered regions, by counting the number of regions of interest for which a given condition is satisfied, said condition relating to the value of the regional diffusion coefficient associated with the region under consideration, relative to a reference regional coefficient which is equal to an average of the regional diffusion coefficient for this region for a cohort of healthy patients; and
      a third step of determining said indicator as a function of the number of altered regions.

7. A non-transitory computer readable medium comprising instructions which, when the instructions are executed by a computer, cause the same to implement the steps of the method according to claim 1.

8. The method according to claim 2, wherein, in the second step, the regional diffusion coefficient has moved away from the regional reference coefficient, relative to the initial regional coefficient when a distance between the regional coefficient and the initial regional coefficient is greater than $z_e \cdot \sigma_j$, where $\sigma_j$ is representative of a dispersion of said regional diffusion coefficient, for the region under consideration, for said cohort of healthy patients, and where $z_e$ is a minimum evolution coefficient, between 0.5 and 4.

9. The method according to claim 2, wherein said indicator is representative of an evolutionary nature of said alteration, and wherein in the second step, the number of altered regions is the number of regions with regression of the alteration, a region of interest being considered as a region with regression of the alteration when said condition is that the regional diffusion coefficient has moved closer to the reference regional coefficient, with respect to the initial regional coefficient.

10. The method according to claim 2, for which the date t2 is subsequent to a date of administration of a treatment for brain alteration related to a demyelinating pathology type affliction, and the date t1 is prior to said date of administration of said treatment.

11. The method according to claim 9, wherein, in the second step, the regional diffusion coefficient has moved closer to the regional reference coefficient, with respect to the initial regional coefficient when a distance between the regional coefficient and the initial regional coefficient is greater than $z_e \cdot \sigma_j$, where $\sigma_j$ is representative of a dispersion of said regional diffusion coefficient, for the region under consideration, for said cohort of healthy patients, and where $z_e$ is a minimum evolution coefficient, between 0.5 and 4.

12. The method according to claim 9, wherein the indicator representative of an evolutionary nature of said alteration is all the greater as a difference between the number of regions with progression of the alteration and the number of regions with regression of the alteration is great.

\* \* \* \* \*